United States Patent
Liu et al.

(10) Patent No.: US 10,466,588 B2
(45) Date of Patent: Nov. 5, 2019

(54) SULFONYL PHOTOACID GENERATORS AND PHOTORESISTS COMPRISING SAME

(71) Applicant: Rohm and Haas Electronic Materials LLC, Marlborough, MA (US)

(72) Inventors: Cong Liu, Marlborough, MA (US); Cheng-Bai Xu, Marlborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 15/332,340

(22) Filed: Oct. 24, 2016

(65) Prior Publication Data

US 2017/0153542 A1   Jun. 1, 2017

Related U.S. Application Data

(62) Division of application No. 12/968,130, filed on Dec. 10, 2010, now Pat. No. 9,488,910.

(60) Provisional application No. 61/286,197, filed on Dec. 14, 2009.

(51) Int. Cl.

| | |
|---|---|
| *G03F 7/004* | (2006.01) |
| *G03F 7/30* | (2006.01) |
| *C07C 309/17* | (2006.01) |
| *C07C 311/48* | (2006.01) |
| *C07C 381/12* | (2006.01) |
| *G03F 7/038* | (2006.01) |
| *G03F 7/039* | (2006.01) |
| *C07C 313/04* | (2006.01) |
| *C07C 321/28* | (2006.01) |
| *G03F 7/16* | (2006.01) |
| *G03F 7/20* | (2006.01) |
| *G03F 7/32* | (2006.01) |

(52) U.S. Cl.
CPC .......... *G03F 7/0045* (2013.01); *C07C 309/17* (2013.01); *C07C 311/48* (2013.01); *C07C 313/04* (2013.01); *C07C 321/28* (2013.01); *C07C 381/12* (2013.01); *G03F 7/0046* (2013.01); *G03F 7/0382* (2013.01); *G03F 7/0392* (2013.01); *G03F 7/162* (2013.01); *G03F 7/20* (2013.01); *G03F 7/30* (2013.01); *G03F 7/322* (2013.01); *C07C 2603/74* (2017.05)

(58) Field of Classification Search
CPC ... G03F 7/0045; G03F 7/0046; C07C 309/17; C07C 311/48; C07C 381/12; C07C 303/32

USPC ....... 430/270.1, 326, 921, 922; 562/37, 101, 562/102, 103; 564/80, 82
See application file for complete search history.

(56) References Cited

U.S. PATENT DOCUMENTS

| | | | | |
|---|---|---|---|---|
| 7,960,087 | B2* | 6/2011 | Kodama | G03F 7/0045 430/270.1 |
| 8,557,499 | B2* | 10/2013 | Yamaguchi | G03F 7/0045 430/270.1 |
| 9,488,910 | B2* | 11/2016 | Liu | G03F 7/0045 |
| 2002/0055046 | A1 | 5/2002 | Ono et al. | |
| 2006/0204890 | A1* | 9/2006 | Kodama | G03F 7/0045 430/270.1 |
| 2008/0268370 | A1 | 10/2008 | Tanaka et al. | |
| 2009/0258315 | A1 | 10/2009 | Ober et al. | |
| 2009/0269700 | A1 | 10/2009 | Yonemura et al. | |
| 2011/0008731 | A1 | 1/2011 | Yamaguchi et al. | |

FOREIGN PATENT DOCUMENTS

| | | |
|---|---|---|
| CN | 101231464 A | 7/2008 |
| EP | 1701214 A1 | 9/2006 |
| EP | 1795962 A2 | 6/2007 |
| EP | 1798962 A2 | 6/2007 |
| JP | 2011048111 A | 3/2011 |
| JP | 2011053360 A | 3/2011 |

OTHER PUBLICATIONS

English Language Summary of Office Action issued in counterpart Japanese Application No. 2010-277563, dated Dec. 10, 2014 (8 Pages).
English Language Summary of First Office Action issued in counterpart Chinese Application No. 20140333321.3 (5 Pages).
English Language Summary of Search Report issued in counterpart Chinese Application No. 201410333321.3, dated Dec. 14, 2010 (2 Pages).
English Language Summary of D3, Japanese Publication No. 2011-053360, Published Mar. 17, 2011 (8 Pages).
English Language Summary of D4, Japanese Publication No. 2011-048111, Published Mar. 10, 2011 (4 Pages).
English Language Summary of Korean Application No. 10-2010-0127615 (4 Pages).
Communication pursuant to Article 94(3) EPC for counterpart European Application 10 194 879.2 (9 pages).
Search Report for counterpart European Applicatoin No. 10194879.2 (8 pages).

\* cited by examiner

*Primary Examiner* — John S Chu
(74) *Attorney, Agent, or Firm* — Mintz Levin Cohn Ferris Glovsky and Popeo, P.C.; Peter F. Corless

(57) ABSTRACT

New bis(sulfonyl)imide and tri(sulfonyl)methide photoacid generator compounds ("PAGs") are provided as well as photoresist compositions that comprise such PAG compounds.

13 Claims, No Drawings

SULFONYL PHOTOACID GENERATORS AND PHOTORESISTS COMPRISING SAME

CROSS-REFERENCE TO RELATED APPLICATIONS

This application is a divisional of U.S. patent application Ser. No. 12/968,130, filed Dec. 14, 2010, pending, which claims priority to U.S. Provisional Application No. 61/286,197, filed Dec. 14, 2009, the entire contents of which application are incorporated herein by reference.

This invention relates to new sulfonyl imide and methide photoacid generator compounds ("PAGs") and photoresist compositions that comprise such PAG compounds.

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See, e.g., U.S. Pat. Nos. 6,911,297 and 7,235,343.

In one aspect, we now provide novel photoacid generator compounds (PAGs) that comprise a bis(sulfonyl)imide anon component.

In another aspect, we provide novel photoacid generator compounds (PAGs) that comprise a tris(sulfonyl)methide anion component.

Preferred photoacid generator compounds of the invention comprise an onium component, preferably where a (sulfonyl)imide or (sulfonyl)methide are complexed with an onium cation, such as a sulfonium or iodonium cation.

Preferred photoacid generator compounds of the invention also comprise one or more cyclic groups such as n optionally substituted alicyclic group, optionally substituted carbocyclic group or optionally substituted heteroaromatic group. Such bulky groups preferably are present on the (sulfonyl)imide or (sulfonyl)methide component of the photoacid generator compound Preferred photoacid generator compound also comprise fluoro substitution, including where the (sulfonyl)imide or (sulfonyl)methide is substituted by one 0 or more fluoro atoms.

Preferably, PAGs of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Preferred imaging wavelengths of photoresists of the invention include sub-300 nm wavelengths e.g. 248 nm, and sub-200 nm wavelengths e.g. 193 nm and EUV.

Particularly preferred photoresists of the invention contain an imaging-effective amount of one or more PAGs as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photo acid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups;

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. No. 5,843,624 incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083.

Resists of the invention also may comprise a mixture of distinct PAGs, typically a mixture of 2 or 3 different PAGs, more typically a mixture that consists of a total of 2 distinct PAGs.

The invention also provide methods for forming relief images of the photoresists of the invention, including methods for forming highly resolved patterned photoresist images (e.g. a patterned line having essentially vertical sidewalls) of sub-quarter micron dimensions or less, such as sub-0.2 or sub-0.1 micron dimensions.

The invention further provides articles of manufacture comprising substrates such as a microelectronic wafer or a flat panel display substrate having coated thereon the photoresists and relief images of the invention. Other aspects of the invention are disclosed infra.

Particularly preferred photoacid generator of the invention include sulfonyl methide compounds of the following Formula I:

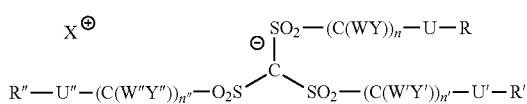

$$\text{I}$$

wherein W, Y are each independently hydrogen, fluorine, optionally substituted fluoroalkyl preferably having 1 to about 20 carbon atoms; optionally substituted fluoroalkoxy preferably having 1 to about 20 carbon atoms; optionally substituted fluorocarbocyclic aryl preferably having 5 to about 20 carbon atoms;

wherein W', Y' are each independently hydrogen, fluorine, optionally substituted fluoroalkyl preferably having 1 to about 20 carbon atoms; optionally substituted fluoroalkoxy preferably having 1 to about 20 carbon atoms; optionally substituted fluorocarbocyclic aryl preferably having 5 to about 20 carbon atoms;

wherein W", Y" are each independently hydrogen, fluorine, optionally substituted fluoroalkyl preferably having 1 to about 20 carbon atoms; optionally substituted fluoroalkoxy preferably having 1 to about 20 carbon atoms; optionally substituted fluorocarbocyclic aryl preferably having 5 to about 20 carbon atoms;

n, n' and n" are each the same or different and are each a positive integer preferably from 1 to 15, more preferably 1 to 6, more preferably n, n' and/or n" are independently 1, 2 or 3;

U, U' and U" are each the same or different and are each a linker such as a chemical bond, optionally substituted alkylene (e.g. $(-CH_2-)_n$ were n is 1 to about 20 and each methylene may be substituted by one or two atoms other than hydrogen such as halo, cyano, $C_{1-20}$alkyl, $C_{1-20}$alkoxy, carbocyclic aryl, and the like, and the carbon chain may have one or more interposed hetero (N, O, S) atoms); and R, R' and R" each the same or different and are each an optionally substituted carboalicyclic (non-aromatic ring where all ring members are carbon), optionally substituted heteroalicyclic (non-aromatic ring where one or more ring members are hetero (N, O or S) atoms in addition to carbon ring members), optionally substituted carbocyclic aryl (aromatic ring where all ring members are carbon), or heteroaromatic group (aromatic ring where one or more ring members are hetero (N, O or S) atoms in addition to carbon ring members) having 3 to 20, 30 or 40 carbon atoms and optionally zero, one or more ring heteroatoms (N, O, or S), wherein R, R' and R" each may be independently monocyclic or have one or more linked (including fused) rings;

$X^+$ is a counter ion, preferably an organic counter ion, in particular an onium compound such as a sulfonium or iodonium compound.

In Formula I above, preferably at least one of or both of W and Y are fluoro or fluoroalkyl especially perfluoroalkyl such as $-CF_3$; and/or preferably at least one of or both of W' and Y' are fluoro or fluoroalkyl especially perfluoroalkyl such as $-CF_3$; and/or preferably at least one of or both of W" and Y" are fluoro or fluoroalkyl especially perfluoroalkyl such as $-CF_3$.

For certain preferred photoacid generators, in Formula I, $-C(WY)_n)-U-R$ and $-C(W'Y')_{n'})-U'-R'$, and $-C(W"Y")_{n"})-U"-R"$ are each the same.

For certain other preferred photoacid generators, in Formula I, no more than two of $-C(WY)_n)-U-R$ and $-C(W'Y')_{n'})-U'-R'$, and $-C(W"Y")_{n"})-U"-R"$ are the same.

For still other preferred photoacid generators, in Formula I, each of $-C(WY)_n)-U-R$ and $-C(W'Y')_{n'})-U'-R'$, and $-C(W"Y")_{n"})-U"-R"$ are different.

For certain other preferred photoacid generators, in Formula II, $-C(WY)_n)-U-R$ and $-C(W'Y')_{n'})-U'-R'$ are different Additional particularly preferred photoacid generator of the invention include sulfonyl imide compounds of the following Formula II:

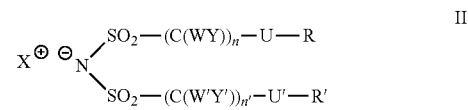

$$\text{II}$$

wherein W, Y are each independently hydrogen, fluorine, optionally substituted fluoroalkyl preferably having 1 to about 20 carbon atoms; optionally substituted fluoroalkoxy preferably having 1 to about 20 carbon atoms; optionally substituted fluorocarbocyclic aryl preferably having 5 to about 20 carbon atoms;

wherein W', Y' are each independently hydrogen, fluorine, optionally substituted fluoroalkyl preferably having 1 to about 20 carbon atoms; optionally substituted fluoroalkoxy preferably having 1 to about 20 carbon atoms; optionally substituted fluorocarbocyclic aryl preferably having 5 to about 20 carbon atoms;

n and n' are each the same or different and are each a positive integer preferably from 1 to 15, more preferably 1 to 6, more preferably n and/or n" are independently 1, 2 or 3;

U and U' are each the same or different and are each a linker such as a chemical bond, optionally substituted alkylene (e.g. $(-CH_2-)_n$ were n is 1 to about 20 and each methylene may be substituted by one or two atoms other than hydrogen such as halo, cyano, $C_{1-20}$alkyl, $C_{1-20}$alkoxy, carbocyclic aryl, and the like, and the carbon chain may have one or more interposed hetero (N, O, S) atoms); and R and R' are each the same or different and are each an optionally substituted carboalicyclic (non-aromatic ring where all ring members are carbon), optionally substituted heteroalicyclic (non-aromatic ring where one or more ring members are hetero (N, O or S) atoms in addition to carbon ring members), optionally substituted carbocyclic aryl (aromatic ring where all ring members are carbon), or optionally substituted heteroaromatic group (aromatic ring where one or more ring members are hetero (N, O or S) atoms in addition to carbon ring members) having 3 to 20, 30 or 40 ring carbon atoms and optionally zero, one or more ring heteroatoms (N, O, or S), wherein R and R' may be independently monocyclic or have one or more linked (including fused) rings;

$X^+$ is a counter ion, c preferably an organic counter ion, in particular an preferably an onium compound such as a sulfonium or iodonium compound.

In Formula II above, preferably at least one of or both of W and Y are fluoro or fluoroalkyl especially perfluoroalkyl such as $-CF_3$; and/or preferably at least one of or both of W' and Y' are fluoro or fluoroalkyl especially perfluoroalkyl such as $-CF_3$.

For certain preferred photoacid generators, in Formula H, $-C(WY)_n)-U-R$ and $-C(W'Y')_{n'})-U'-R'$ are the same.

For certain other preferred photoacid generators, in Formula II, $-C(WY)_n)-U-R$ and $-C(W'Y')_{n'})-U'-R'$ are different.

In the above Formulae I and II, fR, R' and R" may be a cyclic group. A wide variety of groups will be suitable including non-aromatic and aromatic such as optionally substituted adamantyl, optionally substituted norbornyl, optionally substituted phenyl, optionally substituted naphthyl, optionally substituted cyclic structures having hetero (N, O or S) ring members such as lactones, and the like. Ibn certain embodiments, preferred are groups that comprise multiple rings such as where 2, 3, 4, 5 or more rings are linked including fused as well as saturated cage structures.

In the above Formulae I and II, suitable X+ cations may be a variety of compounds with preferred groups including the following:

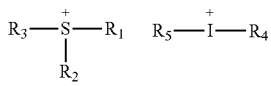

where $R_1$ to $R_5$ each independently represents C1-16 optionally substituted alkyl group or a substituted or unsubstituted carbocyclic aryl group such as phenyl, naphthyl, etc., or any two or more of $R_1$, $R_2$ and $R_3$ may bond together to form a ring with the sulfur ring (e.g. a 5, 6 or 7 membered ring with the sulfur atom). A preferred example of the carbocyclic aryl group includes a $C_{6-14}$ monocyclic or a condensed ring aryl group. Preferred examples of the substituent on the aryl group include an alkyl group, a haloalkyl group, a cycloalkyl group, an aryl group, an alkoxy group, a nitro group, a carboxyl group, an alkoxycarbonyl group, a hydroxyl group, mercapto group, and a halogen atom.

Even more preferred cation components of PAGs of the invention include compounds of any of the following formulae IIa, IIb, IIc or IId:

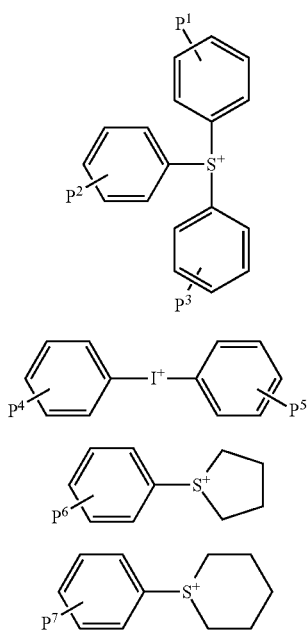

wherein in those formulae $P^1$, $P^2$, $P^3$, $P^4$, $P^5$, $P^6$, and $P^7$ each independently represent hydrogen or one to five non-hydrogen substituents such as hydroxyl, halo, cyano, optionally substituted alkyl group having 1 to 12 carbon atoms or optionally substituted alkoxy group having 1 to 12 carbon atoms.

Specifically preferred PAGs of the invention include the following:

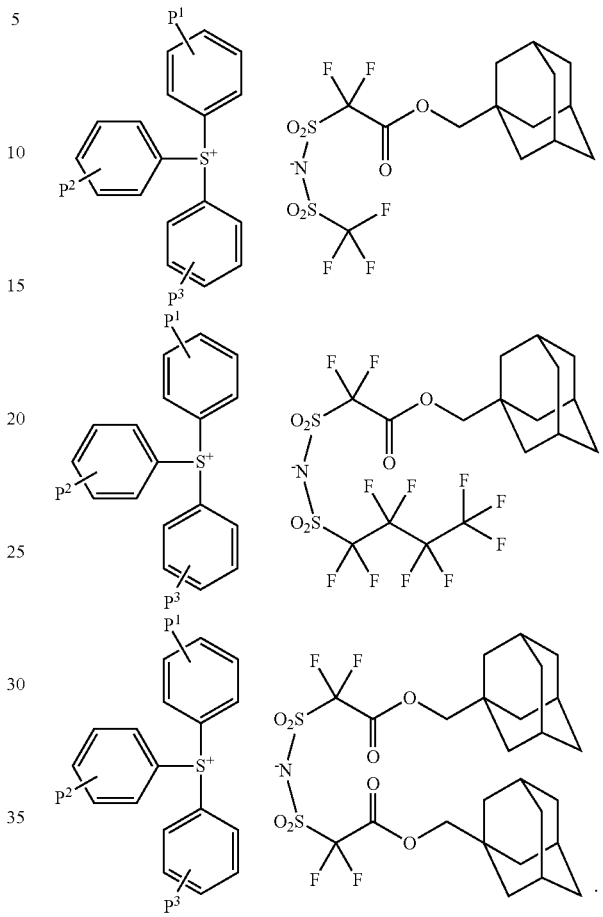

wherein in those formulae $P^1$, $P^2$, $P^3$, $P^4$, $P^5$, $P^6$, and $P^7$ each independently represent hydrogen or one to five non-hydrogen substituents such as hydroxyl, halo, cyano, optionally substituted alkyl group having 1 to 12 carbon atoms or optionally substituted alkoxy group having 1 to 12 carbon atoms. It is understood that by stating that a P substituent (e.g. $P^1$) represents more than one non-hydrogen substituent that indicates that more than one non-hydrogen substituent is present on the particular phenyl ring.

Additional specifically preferred photoacid generator compounds of the invention include the following:

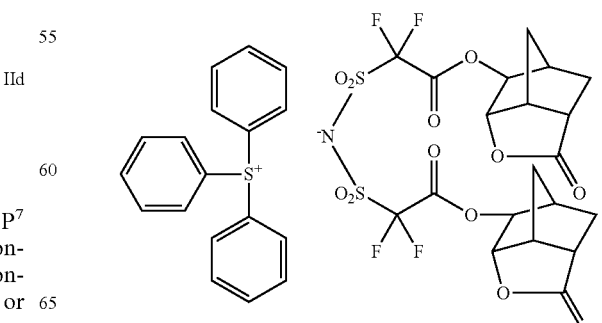

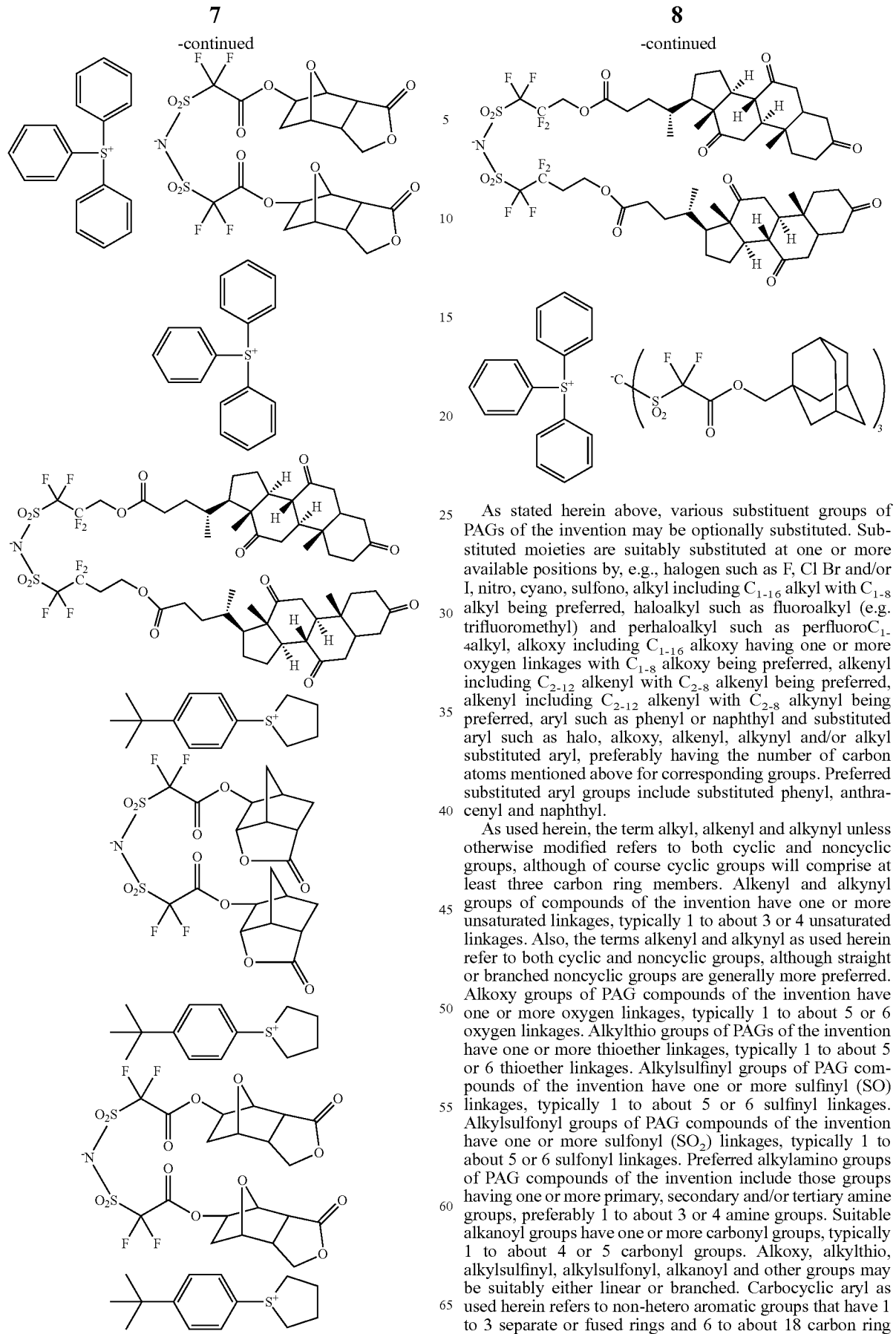

As stated herein above, various substituent groups of PAGs of the invention may be optionally substituted. Substituted moieties are suitably substituted at one or more available positions by, e.g., halogen such as F, Cl Br and/or I, nitro, cyano, sulfono, alkyl including $C_{1-16}$ alkyl with $C_{1-8}$ alkyl being preferred, haloalkyl such as fluoroalkyl (e.g. trifluoromethyl) and perhaloalkyl such as perfluoro$C_{1-4}$alkyl, alkoxy including $C_{1-16}$ alkoxy having one or more oxygen linkages with $C_{1-8}$ alkoxy being preferred, alkenyl including $C_{2-12}$ alkenyl with $C_{2-8}$ alkenyl being preferred, alkenyl including $C_{2-12}$ alkenyl with $C_{2-8}$ alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthracenyl and naphthyl.

As used herein, the term alkyl, alkenyl and alkynyl unless otherwise modified refers to both cyclic and noncyclic groups, although of course cyclic groups will comprise at least three carbon ring members. Alkenyl and alkynyl groups of compounds of the invention have one or more unsaturated linkages, typically 1 to about 3 or 4 unsaturated linkages. Also, the terms alkenyl and alkynyl as used herein refer to both cyclic and noncyclic groups, although straight or branched noncyclic groups are generally more preferred. Alkoxy groups of PAG compounds of the invention have one or more oxygen linkages, typically 1 to about 5 or 6 oxygen linkages. Alkylthio groups of PAGs of the invention have one or more thioether linkages, typically 1 to about 5 or 6 thioether linkages. Alkylsulfinyl groups of PAG compounds of the invention have one or more sulfinyl (SO) linkages, typically 1 to about 5 or 6 sulfinyl linkages. Alkylsulfonyl groups of PAG compounds of the invention have one or more sulfonyl ($SO_2$) linkages, typically 1 to about 5 or 6 sulfonyl linkages. Preferred alkylamino groups of PAG compounds of the invention include those groups having one or more primary, secondary and/or tertiary amine groups, preferably 1 to about 3 or 4 amine groups. Suitable alkanoyl groups have one or more carbonyl groups, typically 1 to about 4 or 5 carbonyl groups. Alkoxy, alkylthio, alkylsulfinyl, alkylsulfonyl, alkanoyl and other groups may be suitably either linear or branched. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S), Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, and benzothiazole.

Photoacid generator compounds of the invention may be readily prepared as generally depicted in the following Schemes.

In particular, the following Scheme 1 exemplifies synthesis of a preferred bis(sulfonyl)imide complexed with triphenylsulfonium (TPS) cation.

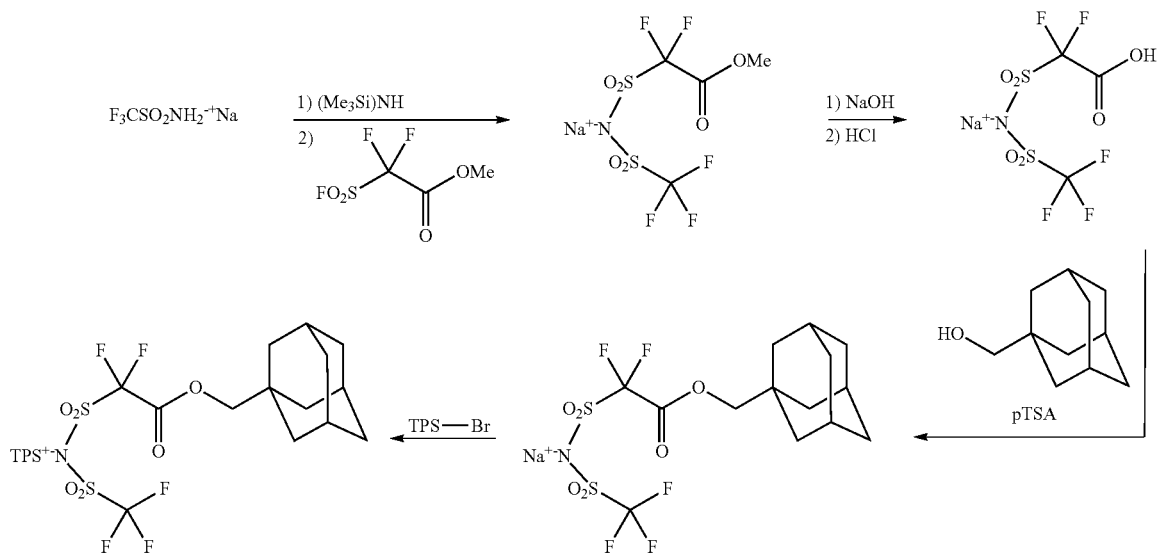

The following Scheme 2 exemplifies synthesis of another preferred bis(sulfonyl)imide complexed with triphenylsulfonium (TPS) cation.

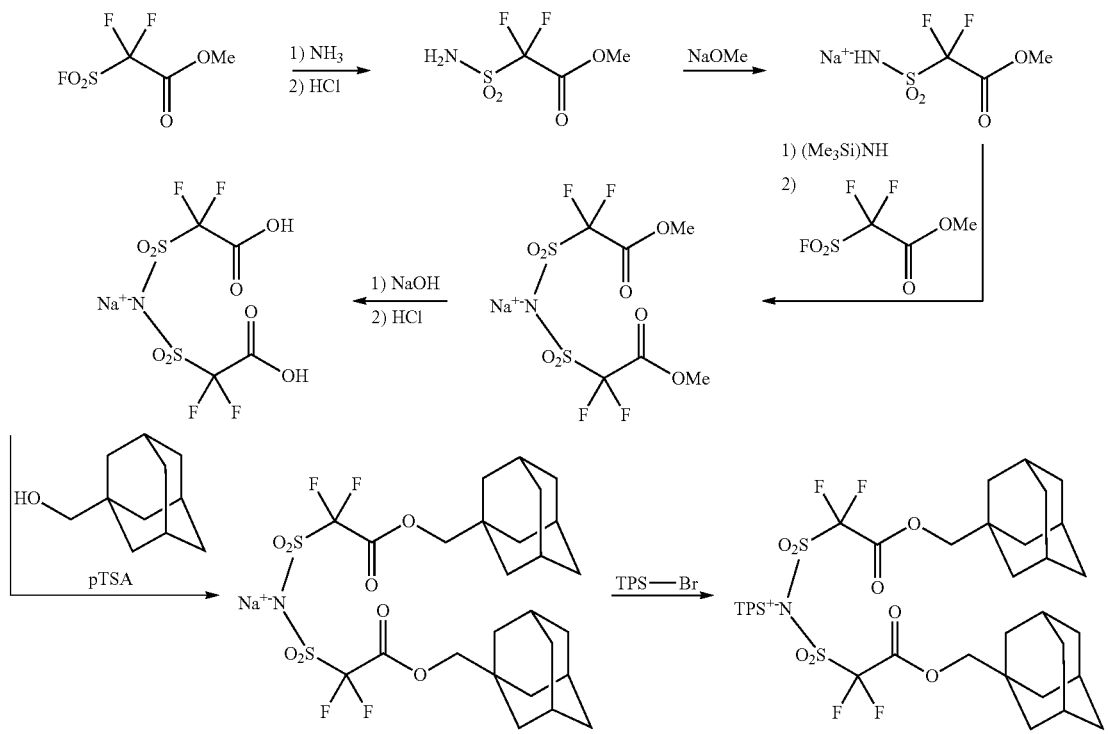

The following Scheme 3 exemplifies synthesis of a preferred tris(sulfonyl)methide complexed with triphenylsulfonium (TPS) cation.

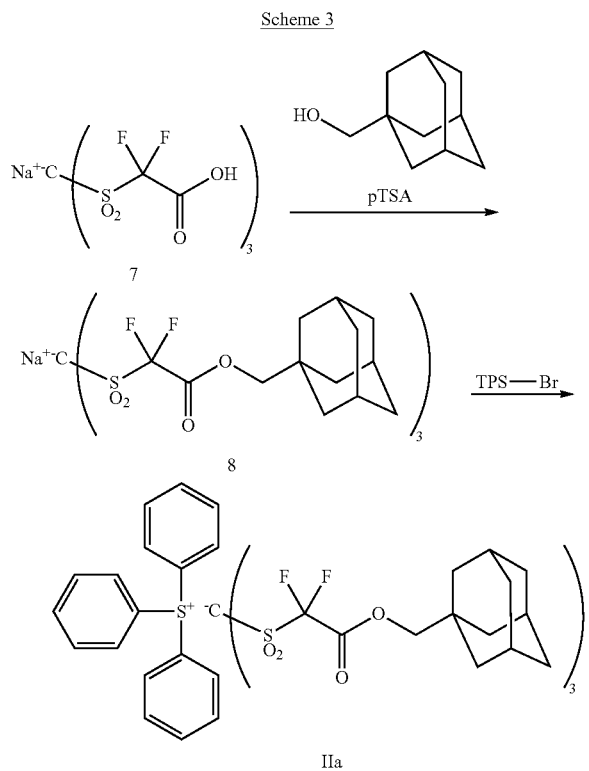

Scheme 3

As discussed above, PAGs of the invention are useful as the radiation sensitive component in photoresist compositions, including both positive-acting and negative-acting chemically amplified resist compositions.

The photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution.

Preferably, a photoacid generator compound of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

PAGs of the invention also are preferably used with polymers that contain one or more photoacid-labile groups and that are substantially, essentially or completely free of phenyl or other aromatic groups. Such photoresist compositions are particularly useful for imaging with sub-200 nm radiation such as 193 nm radiation.

For example, preferred polymers contain less than about 5 mole percent aromatic groups, more preferably less than about 1 or 2 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged with such short wavelength radiation.

Suitable polymers that are substantially or completely free of aromatic groups and may be formulated with a PAG of the invention to provide a photoresist for sub-200 nm imaging are disclosed in European application EP930542A1 of the Shipley Company.

Suitable polymers that are substantially or completely free of aromatic groups suitably contain acrylate units such as photoacid-labile acrylate units as may be provided by polymerization of methyladamanatylacrylate, methyladamanylmethacrylate, ethylfencylacrylate, ethylfencylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride; and the like.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

Photoresists of the invention also may contain other materials. For example, other optional additives include actinic and contrast dyes, anti-striation agents, plasticizers, speed enhancers, sensitizers, etc. Such optional additives typically will be present in minor concentration in a photoresist composition except for fillers and dyes which may be present in relatively large concentrations such as, e.g., in amounts of from 5 to 30 percent by weight of the total weight of a resist's dry components.

A preferred optional additive of resists of the invention is an added base, particularly tetrabutylammonium hydroxide (TBAH), which can enhance resolution of a developed resist relief image. The added base is suitably used in relatively small amounts, e.g. about 1 to 10 percent by weight relative to the PAG, more typically 1 to about 5 weight percent. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; propionates, particularly methyl propionate and ethyl propionate; a Cellosolve ester such as methyl Cellosolve acetate; an aromatic hydrocarbon such toluene or xylene; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 1 to 300 mJ/cm$^2$. As discussed above, preferred exposure wavelengths include sub-200 nm such as 193 nm. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The following non-limiting examples are illustrative of the invention. All documents mentioned herein are incorporated herein by reference in their entirety.

EXAMPLE 1: SYNTHESIS OF SULFONYL IMIDE PHOTOACID GENERATOR (COMPOUND 1C)

The triphenylsulonium bis(sulfonyl)imide photoacid generator shown as Compound 1c un the Scheme below is prepared as shown in the following Scheme and as set forth in the following experimental. In the following experimentals, references to various compound numbers are to those structures shown in the Scheme immediately below.

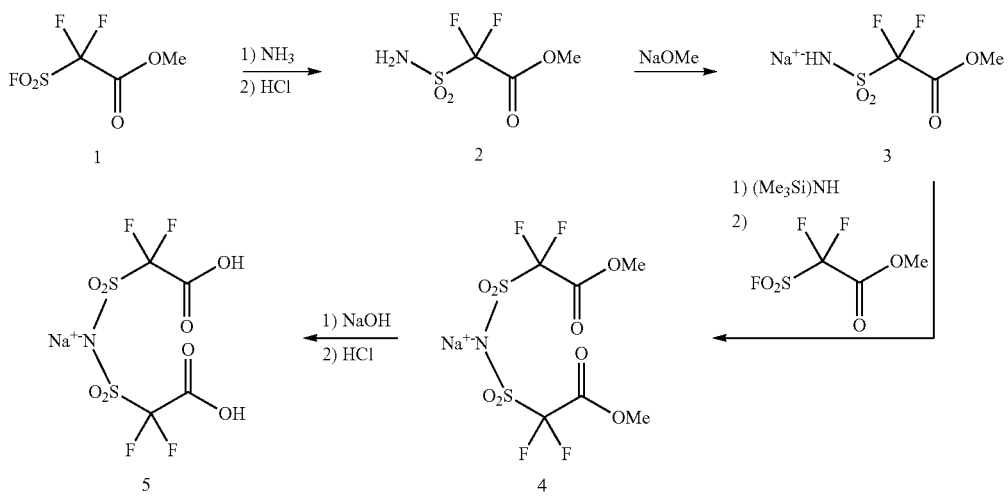

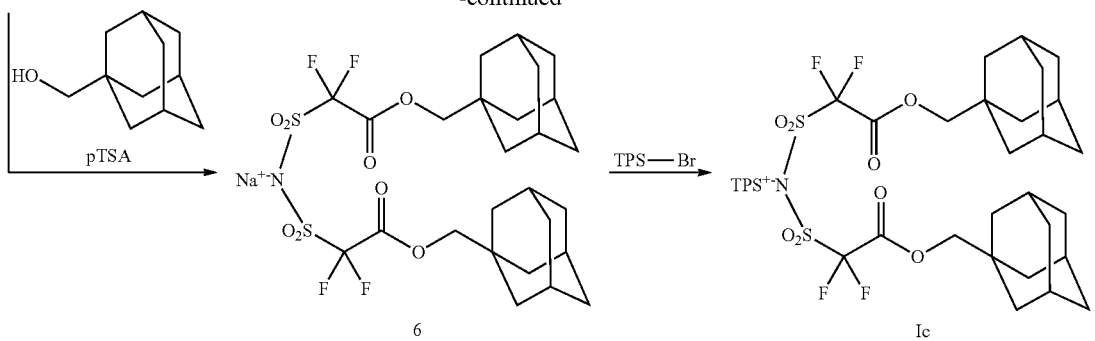

Experimentals

Part 1: Synthesis of Compound 2

2,2-Difluoro-2-methoxycarbonylmethanesulfonyl fluoride (192 parts) is dissolved in anhydrous THF (576 parts) and cooled in ice bath. Ammonia is bubbled into the solution until the reaction mixture becomes basic. Hydrochloric acid (6M) is added dropwise until pH 1. The solvent is removed to give Compound 2.

Part 2: Synthesis of Compound 3

Compound 2 (189 parts) is dissolved in NaOMe/MeOH solution. The mixture is heated to reflux for 18 hr and cooled in ice bath. Compound 3 is used in next step without purification.

Part 3: Synthesis of Compound 4

Mixture from above is treated with hexamethyldisilazine (161 parts) and 2,2-difluoro-2-methoxycarbonylmethanesulfonyl fluoride (192 parts) sequentially to give Compound 4, which is used in next step without purification.

Part 4: Synthesis of Compound 5

Sodium hydroxide (120 parts) is added to the above mixture. The resulting mixture is heated to reflux for 10 hr and cooled in ice bath. Hydrochloric acid (6M) is added dropwise until pH 1. The solvent is removed to give Compound 5.

Part 5: Synthesis of Compound 6

A mixture of compound 5 (355 parts), 1-adamantane methanol (166 parts), pTSA (3,6 parts) in toluene is heated to reflux for 18 hr and cooled to room temperature. The mixture is filtered. The solids are extracted with acetonitrile three times. The combined acetonitrile solution is concentrated to small volume and added dropwise to MTBE. The mixture is filtered and the solids are dried to give Compound 6.

EXAMPLE 2: SYNTHESIS OF SULFONYL METHIDE PHOTOACID GENERATOR

The triphenylsulonium tris(sulfonyl)methide photoacid generator shown as Compound IIc is prepared as shown in the following Scheme and as set forth in the following experimental. In the following experimentals, references to various compound numbers are to those structures shown in the Scheme immediately below.

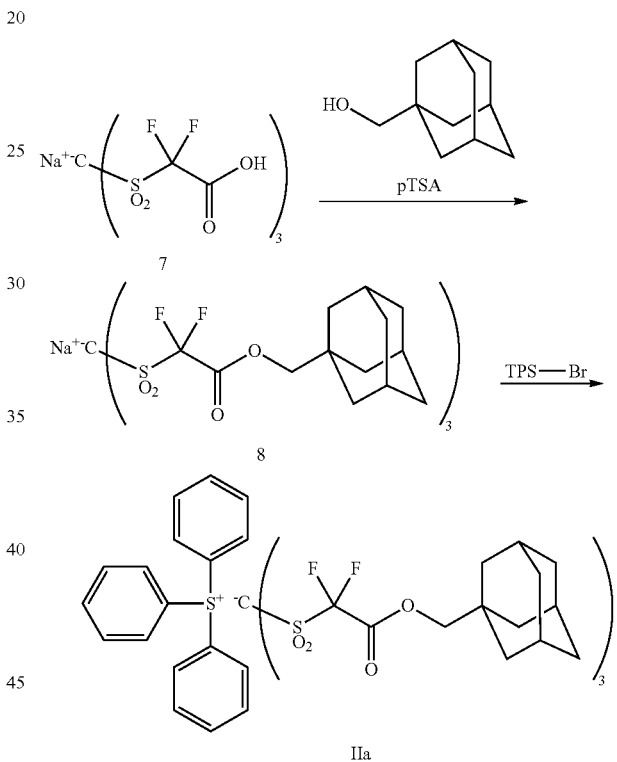

Experimentals

Part 1. Synthesis of Compound 8

A mixture of compound 7 (512 parts), 1-adamantane methanol (166 parts), pTSA (3.6 parts) in toluene is heated to reflux for 18 hr and cooled to room temperature. The mixture is filtered. The solids are extracted with acetonitrile three times. The combined acetonitrile solution is concentrated to small volume and added dropwise to MTBE. The mixture is filtered and the solids are dried to give Compound 8.

Part 2. Synthesis of Compound 1c

Compound 6 (957 parts) and triphenylsulfonium bromide (343 parts) are dissolved in mixed solvent of methylene chloride and water. The mixture is stirred at room temperature for 24 hr. Aqueous workup gives photoacid generator Compound IIa.

EXAMPLE 3: PHOTORESIST PREPARATION AND LITHOGRAPHIC PROCESSING

A photoresist of the invention is prepared by mixing the following components with amounts expressed as weight percent based on total weight of the resist compositions:

| Resist components | Amount (wt. %) |
|---|---|
| Resin binder | 15 |
| Photoacid generator | 4 |
| Basic additive | 0.17 |
| Ethyl lactate | balance |

The resin binder is a terpolymer (2-methyl-2-adamantyl methacrylate/beta-hydroxy-gamma-butyrolactone methacrylate/cyano-norbornyl methacrylate. The photoacid generator is the photoacid generator of compound of Example 1 above (Compound 6 in that Example 1). The basic additive is N-alkyl caprolactam. Those resin, PAG and basic additive components are admixed in the ethyl lactate solvent.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26N aqueous tetramethylammonium hydroxide solution to develop the imaged resist layer.

EXAMPLE 4: PHOTORESIST PREPARATION AND LITHOGRAPHIC PROCESSING

A photoresist of the invention is prepared by mixing the following components with amounts expressed as weight percent based on total weight of the resist compositions:

| Resist components | Amount (wt. %) |
|---|---|
| Resin binder | 13 |
| Photoacid generator | 3 |
| Basic additive | 0.15 |
| Ethyl lactate | balance |

The resin binder is a terpolymer (2-methyl-2-adamantyl methacrylate/beta-hydroxy-gamma-butyrolactene methacrylate/cyano-norbornyl methacrylate. The photoacid generator is the photoacid generator of compound of Example 1 above (Compound 6 in that Example IIc). The basic additive is N-alkyl caprolactam. Those resin, PAG components and basic additive are admixed in the ethyl lactate solvent.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26N aqueous tetramethylammonium hydroxide solution to develop the imaged resist layer.

What is claimed is:

1. A photoacid generator compound of the following Formula I:

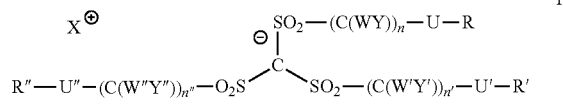

wherein W, Y are each independently hydrogen, fluorine, optionally substituted fluoroalkyl;
optionally substituted fluoroalkoxy; or optionally substituted fluorocarbocyclic aryl;
W', Y' are each independently the same as defined for W and Y;
W", Y" are each independently the same as defined for W and Y;
n, n' and n" are each the same or different and are each a positive integer;
U, U' and U" are each the same or different and are each a linker; and
R, R' and R" are each the same or different and are each an optionally substituted carboalicyclic, optionally substituted heteroalicyclic, optionally substituted carbocyclic aryl, or optionally substituted heteroaromatic group;
$X_+$ is a sulfonium or iodonium group.

2. A photoacid generator compound of the following Formula II:

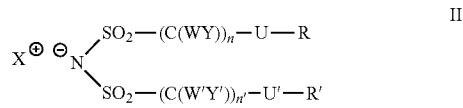

wherein W, Y are each independently hydrogen, fluorine, optionally substituted fluoroalkyl;
optionally substituted fluoroalkoxy; or optionally substituted fluorocarbocyclic aryl;
W', Y' are each independently the same as defined for W and Y;
n and n' are each the same or different and are each a positive integer;
U and U' are each the same or different and are each a linker; and
R and R' are each the same or different and are each an optionally substituted carboalicyclic, optionally substituted heteroalicyclic, optionally substituted carbocyclic aryl, or optionally substituted heteroaromatic group;
$X_+$ is a sulfonium or iodonium group.

3. A photoacid generator of claim 1 wherein $X_+$ is of either of the following formulae:

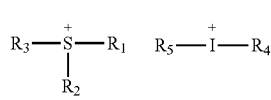

where $R_1$ to $R_5$ each independently represents $C_{1-30}$ optionally substituted alkyl group or a substituted or unsubstituted carbocyclic aryl group, or any two or more of $R_1$, $R_2$ and $R_3$ may bond together to form a ring with the sulfur ring.

4. A photoacid generator compound of claim 1 wherein $X_+$ is any of the following groups:

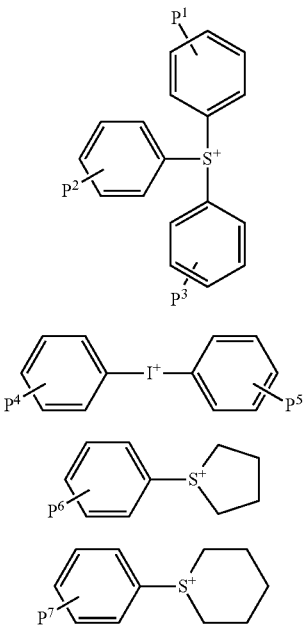

IIa

IIb

IIc

IId wherein in those formulae $P_1$, $P_2$, $P_3$, $P_4$, $P_5$, $P_6$, and $P_7$ each independently represent hydrogen or one to five non-hydrogen substituents.

5. A photoresist composition comprising a photoacid generator compound of claim 1.

6. A method for forming a photoresist relief image comprising:
   a) applying a coating layer of a photoresist composition of claim 5 on a substrate;
   b) exposing the photoresist coating layer to patterned activating radiation and developing the exposed photoresist layer to provide a relief image.

7. A photoresist composition comprising a photoacid generator compound of claim 3.

8. A method for forming a photoresist relief image comprising:
   a) applying a coating layer of a photoresist composition of claim 7 on a substrate;
   b) exposing the photoresist coating layer to patterned activating radiation and developing the exposed photoresist layer to provide a relief image.

9. A photoresist composition comprising a photoacid generator compound of claim 4.

10. A method for forming a photoresist relief image comprising:
    a) applying a coating layer of a photoresist composition of claim 9 on a substrate;
    b) exposing the photoresist coating layer to patterned activating radiation and developing the exposed photoresist layer to provide a relief image.

11. A photoacid generator of claim 2 wherein $X_+$ is a sulfonium compound.

12. A photoacid generator of claim 2 wherein $X_+$ is of either of the following formulae:

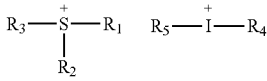

where $R_1$ to $R_5$ each independently represents $C_{1-30}$ optionally substituted alkyl group or a substituted or unsubstituted carbocyclic aryl group, or any two or more of $R_1$, $R_2$ and $R_3$ may bond together to form a ring with the sulfur ring.

13. A photoacid generator compound of claim 1 wherein $X_+$ is any of the following groups:

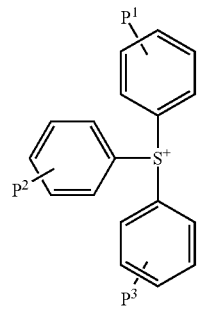

IIa

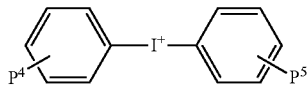

IIb

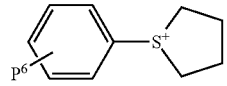

IIc

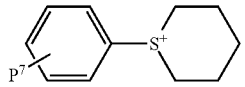

IId wherein in those formulae $P_1$, $P_2$, $P_3$, $P_4$, $P_5$, $P_6$, and $P_7$ each independently represent hydrogen or one to five non-hydrogen substituents.

* * * * *